United States Patent [19]

Tomotsu et al.

[11] Patent Number: 5,093,295
[45] Date of Patent: Mar. 3, 1992

[54] PROCESS FOR PRODUCING HOMOGENEOUS ALUMINOXANE SOLUTION

[75] Inventors: Norio Tomotsu; Masahiko Kuramoto, both of Ichihara, Japan

[73] Assignee: Idemitsu Kosan Company Limited, Tokyo, Japan

[21] Appl. No.: 490,338

[22] Filed: Mar. 8, 1990

[30] Foreign Application Priority Data

Mar. 23, 1989 [JP] Japan .................................. 1-69305

[51] Int. Cl.$^5$ .............................................. C08F 4/62
[52] U.S. Cl. ...................................... 502/152; 502/103; 502/117; 556/179
[58] Field of Search ...................... 502/152, 103, 117; 556/179

[56] References Cited

U.S. PATENT DOCUMENTS

| | | | |
|---|---|---|---|
| 4,544,762 | 10/1985 | Kaminsky et al. | 556/179 |
| 4,552,859 | 11/1985 | Band et al. | 502/127 |
| 4,701,432 | 10/1987 | Welborn, Jr. | 502/113 |

FOREIGN PATENT DOCUMENTS 0232595 8/1987 European Pat. Off. .

OTHER PUBLICATIONS

Journal of Polymer Science/Part A: Polymer Chemistry, vol. 26, No. 11, Oct. 1988, pp. 3089-3102, "Metallocene-Methylaluminoxane Catalysts for Olefin Polymerization. I. Trimethylaluminum as Coactivator".

Primary Examiner—Patrick P. Garvin
Assistant Examiner—Brent M. Peebles
Attorney, Agent, or Firm—Frishauf, Holtz, Goodman & Woodward

[57] ABSTRACT

The present invention provides a process for producing a homogeneous aluminoxane solution wherein an alkylaminoxane (A) obtained by reacting an organoaluminum compound with water and removing a solid residue by filtration is reacted with an organoaluminum compound (C) in the presence of an aromatic hydrocarbon solvent (B). According to the present invention, the gel-free homogeneous aluminoxane solution can be obtained and the catalytic activity thereof is not deteriorated during the storage.

12 Claims, No Drawings

PROCESS FOR PRODUCING HOMOGENEOUS ALUMINOXANE SOLUTION

BACKGROUND OF THE INVENTION

The present invention relates to a process for producing an aluminoxane solution usable as a catalyst in the production of syndiotactic polystyrene (SPS) or as an olefinpolymerization catalyst. In particular, the present invention relates to a homogeneous aluminoxane solution free from gel components and highly active as a catalyst component.

An alkylaluminoxane obtained by reacting an organoaluminum compound with water has been used as a catalyst component in the polymerization of an olefin, styrene or the like. The alkylaluminoxane used as the catalyst component is produced by reacting an organoaluminum compound with water, drying the reaction product to form a glassy solid and adding an aromatic solvent thereto.

However, the aluminoxane has a problem that since it is a condensate, it is apt to form an associated molecule and particularly when its molecular weight is high, it is difficultly soluble in an organic solvent. Another problem of the aluminoxane is that a gel is formed and precipitated in the solution during the storage or it is deposited on the vessel wall. Since the gel is viscous and difficultly dispersed, a uniform catalyst solution cannot be obtained. Therefore, the catalyst concentration becomes uneven or pipes are clogged during the storage or transportation through a line.

SUMMARY OF THE INVENTION

After intensive investigations made for the purpose of solving the above-described problems, the inventors have developed a process for producing a homogeneous solution of an alkylaluminoxane having a high catalytic activity, the solution being free from gel components and suitable for the transportation through a line. The present invention has been completed on the basis of this finding.

The present invention provides a process for producing a homogeneous aluminoxane solution characterized in that an alkylaminoxane (A) obtained by reacting an organoaluminum compound with water and removing a solid residue by filtration is reacted with an organoaluminum compound (C) in the presence of an aromatic hydrocarbon solvent (B).

DETAILED DESCRIPTION OF THE INVENTION

The alkylaluminoxane used as the component (A) in the present invention is obtained by reacting an organoaluminum compound with water and removing a solid residue by filtration.

The organoaluminum compounds used herein are usually represented by the following general formula:

$$R^1_k Al(OR^2)_m H_p X^1_q \quad (I)$$

wherein $R^1$ and $R^2$ each represent an alkyl group having 1 to 8 carbon atoms, preferably 1 to 4 carbon atoms, $X^1$ represents a halogen atom, k represents a number of $0 < k \leq 3$, m represents a number of $0 \leq m < 3$, p represents a number of $0 \leq p < 3$ and q represents a number of $0 \leq q < 3$, with the proviso that $k+m+p+q$ is 3.

The organoaluminum compounds of the above general formula (I) include, for example, the following compounds: When p and q are 0, the compounds are represented by the general formula: $R^1_k Al(OR^2)_{3-k}$ wherein $R^1$ and $R^2$ are as defined above and k represents a number of preferably $1.5 \leq k \leq 3$. When m and p are 0, the compounds are represented by the general formula: $R^1_k Al X^1_{3-k}$ wherein $R^1$ and $X^1$ are as defined above and k preferably represents a number of $0 < k \leq 3$. When m and q are 0, the compounds are represented by the general formula: $R^1_k AlH_{3-k}$ wherein $R^1$ is as defined above and k preferably represents a number of $2 \leq k \leq 3$. When p is 0, the compounds are represented by the general formula: $R^1_k Al(OR^2)_m X^1_q$ wherein $R^1$, $R^2$ and $X^1$ are as defined above and k, m and q represent numbers of $0 < k \leq 3$, $0 \leq m < 3$ and $0 \leq q < 3$, respectively, with the proviso that the total of k, m and q is 3.

When p and q are 0 and k is 3 in the above general formula (I), the organoaluminum compound is a trialkyl-aluminum such as triethylaluminum, tributylaluminum or a combination of them. It is preferably triethylaluminum, tri-n-butylaluminum or triisobutylaluminum. When p and q are 0 and k is a number of $1.5 \leq k < 3$, the organoaluminum compound is a dialkylaluminum alkoxide such as diethylaluminum ethoxide or dibutylaluminum butoxide; an alkylaluminum sesquialkoxide such as ethylaluminum sesquiethoxide or butylaluminum sesquibutoxide; or a partially alkoxidized alkylaluminum having an average structure of for example, $R^1_{2.5} Al(OR^2)_{0.5}$. When m and p are 0, the organoaluminum compound is a partially halogenated alkylaluminum, that is, for example, a dialkylaluminum halide (k=2) such as diethylaluminum chloride, dibutylaluminum chloride or diethylaluminum bromide; an alkylaluminum sesquihalide (k=1.5) such as ethylaluminum sesquichloride, butylaluminum sesquichloride or ethylaluminum sesquibromide; or an alkylaluminum dihalide (k=1) such as ethylaluminum dichloride, propylaluminum dichloride or butylaluminum dibromide. When m and q are 0, the organoaluminum compound is a partially hydrogenated alkylaluminum, that is, for example, a dialkylaluminum hydride (k=2) such as diethylaluminum hydride or dibutylaluminum hydride; or an alkylaluminum dihydride (m=k) such as ethylaluminum dihydride or propylaluminum dihydride. When p is 0, the compound is a partially alkoxylated and halogenated alkylaluminum such as ethylaluminum ethoxychloride, butylaluminum butoxychloride or ethylaluminum ethoxybromide (k=m=q=1).

Among the above-described organoaluminum compounds, the trialkylaluminums are preferred and trimethylaluminum is particularly preferred.

Water which is reacted with the organoaluminum compound may be ordinary water, ice, vapor or water of various water-containing compounds such as water saturated with a solvent adsorption water of an inorganic substance or metal salt-containing crystal water such as $CuSO_4 \cdot 5H_2O$ or $Al_2SO_4 \cdot nH_2O$.

The alkylaluminoxanes obtained by reacting the abovedescribed organoaluminum compound with water include chain alkylaluminoxanes of the general formula:

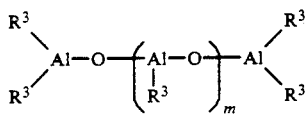

wherein $R^3$ represents an alkyl group having 1 to 8 carbon atoms and m represents a degree of polymerization, and cyclic alkylaluminoxanes comprising recurring units of the general formula:

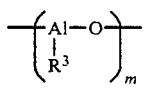

wherein $R^3$ is as defined above.

These alkylaluminoxanes have a molecular weight as determined by cryoscopic method with benzene of 500 to 4,000. The process of the present invention is particularly effective when the alkylaluminoxane having a molecular weight of 1,000 to 4,000 is used since said alkylaluminoxane is apt to form a gel.

The catalytic reaction product of the organoaluminum compound such as the trialkylaluminum with water comprises, in addition to the above-described chain alkylaluminoxane or cyclic alkylaluminoxane, various compounds such as the unreacted trialkylaluminum, a mixture of various condensates and complicated association products of them. Various products are formed from them depending on the conditions of the catalytic reaction of the organoaluminum compound such as the trialkylaluminum with water.

The process for reacting the organoaluminum compound with water is not particularly limited and a known process can be employed. The processes are, for example, (1) process wherein the organoaluminum compound is dissolved in an organic solvent and the solution thus obtained is brought into contact with water and (2) a process wherein crystal water contained in the metal salt or the like, or adsorption water of an inorganic or organic substance is reacted with the organoaluminum compound. Although this reaction proceeds even in the absence of any solvent, it is preferably conducted in a solvent. The solvents suitably used include aliphatic hydrocarbons such as hexane heptane and decane, and aromatic hydrocarbons such as benzene, toluene, xylene ethylbenzene and cumene.

The alkylaluminoxane used as the component (A) in the present invention is obtained by removing, by filtration, a solid residue such as the metal salt of the water-containing compound after the catalytic reaction and, if necessary, removing a volatile component therefrom.

In the present invention, the alkylaluminoxane (A) is reacted with the organoaluminum compound (C) in the presence of an aromatic hydrocarbon solvent (B).

The aromatic hydrocarbon solvents (B) used herein include, for example, benzene, toluene, ethylbenzene, xylene and cumene.

The organoaluminum compounds (C) are those represented by the above general formula (I). Among them, those having a branched alkyl group having 3 to 9 carbon atoms such as isobutyl group are preferred.

Usually in the process of the present invention, the aromatic hydrocarbon solvent (B) is added to the alkylaluminoxane (A), then the organoaluminum compound (C) is added thereto and the mixture is stirred to conduct the reaction. The order of the addition is, however, not limited thereto. Namely, both aromatic hydrocarbon solvent (B) and organoalkylaluminum compound (C) can be simultaneously added to the alkylaluminoxane (A) or, alternatively, the organoaluminum compound (C) and then the aromatic hydrocarbon solvent (B) may be added to the alkylaluminoxane (A).

The molar ratio of the organoaluminum compound (C) to the alkylaluminoxane (A) to be reacted is 0.01/1 to 1/1, preferably 0.01/1 to 0.4/1, and more preferably 0.01/1 to 0.09/1 (in terms of aluminum). The concentration of them in the solvent is preferably 0.01 to 5 mol/l (in terms of aluminum).

The reaction is conducted at a temperature ranging from $-40°$ C. to 150° C., preferably from 0° C. to 110° C., under a pressure ranging from reduced pressure to elevated pressure for 1 min to 20 h, preferably 10 min to 2 h.

The homogeneous aluminoxane solution can be thus prepared.

When the aromatic hydrocarbon solvent (B) is added to the alkylaluminoxane (A) and the mixture is left to stand, a gel is formed in the present invention. On the contrary, when the organoaluminum compound (C) is added to the mixture to conduct the reaction, the gel is dissolved to form a gel-free, homogeneous aluminoxane solution.

The aluminoxane solution thus obtained can be used, as it is or in combination with a transition metal compound, as catalyst component in the production of an olefinic polymer such as polyethylene, atactic polypropylene, isotactic polypropylene, syndiotactic polypropylene, polybutene-1 or poly-4-methylpentene-1; ethylene/propylene copolymer; or a styrene polymer having a syndiotactic structure. The transition metal compound is suitably selected from the group consisting of compounds of transition metals of the Groups IVB and VIII of the periodic table depending on the kind of the intended polymer.

The aluminoxane solution prepared by the process of the present invention has an even concentration, it does not adhere to the vessel wall and, therefore, it can be stably transported. The aluminoxane solution obtained by the process of the present invention has a high catalytic activity and it exhibits a particularly high activity in the production of a styrene polymer mainly having syndiotactic structure.

The aluminoxane solution prepared by the process of the present invention forms no gel and its catalytic activity is not deteriorated during the storage.

Thus the homogeneous aluminoxane solution produced by the process of the present invention is effectively usable as a catalyst in the production of an olefinic polymer, styrene polymer or particularly styrene polymer having a syndiotactic structure.

The following Examples will further illustrate the present invention.

EXAMPLE 1

(1) Preparation of alkylaluminoxane:

200 ml of toluene, 23.7 g (95 mmol) of copper sulfate pentahydrate ($CuSO_4.5H_2O$) and 24 ml (250 mmol) of trimethylaluminum were placed in a 500 ml glass vessel in which air had been replaced with argon, and the reaction was conducted at 40° C. for 30 h. Then a solid thus formed was removed to obtain a solution. Volatile components were distilled off from the solution under reduced pressure to obtain 7.04 g of the catalytic reaction product. The molecular weight of the product as determined by the cryoscopic method in benzene solution was 1100. 60 ml of toluene was added thereto to obtain the alkylaluminoxane solution. After leaving the solution to stand at room temperature for one day, a gel was formed in the form of a precipitate.

(2) Preparation of homogeneous solution

Triisobutylaluminum was added to the gel-containing alkylaluminoxane solution obtained in the above step (1) in a molar ratio of 1:1 (in terms of Al) and the obtained mixture was stirred to dissolve the gel. The gel-free homogeneous solution thus obtained kept its homogeneous state even after one week.

(3) Polymerization of styrene 500 mol of styrene was placed in a 2 l stainless steel autoclave in which air had been replaced with argon. Then 10 mmol (in terms of Al atom) of the aluminoxane solution obtained in the above step (2) was added thereto and then 0.05 mmol of pentamethylcyclopentadienyltitanium trimethoxide as the transition metal compound was added thereto. The polymerization reaction was conducted at 70° C. for 2 h. After completion of the reaction followed by treatment with a hydrochloric acid/methanol solution, washing with methanol and drying, 181 g of a polymer was obtained. The conversion was 40 wt. %. It was confirmed according to $^{13}$C-NMR that this product was a syndiotactic polystyrene having nearly 100% stereospecificity.

EXAMPLE 2

(1) Preparation of alkylaluminoxane

The same procedure as that of Example 1 (1) was repeated except that the reaction temperature and the reaction time were changed to 60° C. and 24 h, respectively.

6.5 g of the catalytic reaction product was obtained. The molecular weight of the product as determined by the cryoscopic method was 1900. 60 ml of toluene was added thereto to obtain the alkylaluminoxane solution. After leaving the solution to stand at room temperature for one day, a gel was formed in the form of a precipitate, which adhered to a part of the vessel wall.

(2) Preparation of homogeneous solution:

Triisobutylaluminum was added to the gel-containing alkylaluminoxane solution obtained in the above step (1) in a molar ratio of 1:1 (in terms of Al) and the obtained mixture was stirred to dissolve the gel. The gel-free homogeneous solution thus obtained kept its homogeneous state even after one week.

(3) Polymerization of styrene

Styrene was polymerized in the same manner as that of Example 1 except that the alkylaluminoxane solution obtained in the above step (2) was used to obtain 220 g of the polymer. The conversion was 48 wt. %. It was confirmed that this product was a syndiotactic polystyrene having nearly 100% stereospecificity.

EXAMPLE 3

(1) Preparation of homogeneous solution

Triisobutylaluminum was added to the gel-containing alkylaluminoxane solution obtained in Example 1 (1) in a molar ratio of 1:0.1 (in terms of Al) and the obtained mixture was stirred to dissolve the gel. The gel-free homogeneous solution thus obtained kept its homogeneous state even after one week.

(2) Polymerization of styrene

Styrene was polymerized in the same manner as that of Example 1 (3) except that the alkylaluminoxane solution obtained in the above step (1) was used to obtain 213 g of the polymer. The conversion was 47.0 wt. %. It was confirmed that this product was a syndiotactic polystyrene having nearly 100% stereospecificity.

EXAMPLE 4

(1) Preparation of homogeneous solution

Triisobutylaluminum was added to the gel-containing alkylaluminoxane solution obtained in Example 2 (1) in a molar ratio of 1:0.08 (in terms of Al) and the obtained mixture was stirred to dissolve the gel. The gel-free homogeneous solution thus obtained kept its homogeneous state even after one week.

(2) Polymerization of styrene

Styrene was polymerized in the same manner as that of Example 2 (3) except that the alkylaluminoxane solution obtained in the above step (1) was used to obtain 261 g of the polymer. The conversion was 57.6 wt. %. It was confirmed that this product was a syndiotactic polystyrene having nearly 100% stereospecificity.

EXAMPLE 5

(1) Preparation of homogeneous solution

Triisobutylaluminum was added to the gel-containing alkylaluminoxane solution obtained in Example 1 (1) in a molar ratio of 1:0.02 (in terms of Al) and the obtained mixture was stirred to dissolve the gel. The gel-free homogeneous solution thus obtained kept its homogeneous state even after one week.

(2) Polymerization of styrene

Styrene was polymerized in the same manner as that of Example 1 (3) except that the alkylaluminoxane solution obtained in the above step (1) was used to obtain 230 g of the polymer. The conversion was 50.1 wt. %. It was confirmed that this product was a syndiotactic polystyrene having nearly 100% stereospecificity.

EXAMPLE 6

(1) Preparation of homogeneous solution

Triethylaluminum was added to the gel-containing alkylaluminoxane solution obtained in Example 1 (1) in a molar ratio of 1:0.08 (in terms of Al) and the obtained mixture was stirred to dissolve the gel. The gel-free homogeneous solution thus obtained kept its homogeneous state even after one week.

(2) Polymerization of styrene

Styrene was polymerized in the same manner as that of Example 1 (3) except that the alkylaluminoxane solution obtained in the above step (1) was used to obtain 223 g of the polymer. The conversion was 48.6 wt. %. It was confirmed that this product was a syndiotactic polystyrene having nearly 100% stereospecificity.

EXAMPLE 7

(1) Preparation of homogeneous solution

Diethylaluminum ethoxide was added to the gel-containing alkylaluminoxane solution obtained in Example 1 (1) in a molar ratio of 1:0.1 (in terms of Al) and the obtained mixture was stirred to dissolve the gel. The gel-free homogeneous solution thus obtained kept its homogeneous state even after one week.

(2) Polymerization of styrene

Styrene was polymerized in the same manner as that of Example 1 (3) except that the alkylaluminoxane solution obtained in the above step (1) was used to obtain 218 g of the polymer. The conversion was 47.5 wt. %. It was confirmed that this product was a syndiotactic polystyrene having nearly 100% stereospecificity.

EXAMPLE 8

(1) Preparation of homogeneous Solution

Diethylaluminum chloride was added to the gel-containing alkylaluminoxane solution obtained in Example 1 (1) in a molar ratio of 1:0.1 (in terms of Al) and the obtained mixture was stirred to dissolve the gel. The gel-free homogeneous solution thus obtained kept its homogeneous state even after one week.

(2) Polymerization of styrene

Styrene was polymerized in the same manner as that of Example 1 (3) except that the alkylaluminoxane solution obtained in the above step (1) was used to obtain 212 g of the polymer. The conversion was 46.2 wt. %. It was confirmed that this product was a syndiotactic polystyrene having nearly 100% stereospecificity.

What is claimed is:

1. A process for producing an homogeneous aluminoxane solution free of gel components comprising
reacting an organoaluminum compound with water to form an alkylaluminoxane (A);
filtering the alkylaluminoxane (A) to remove any solid residue; and thereafter
mixing the alkylaluminoxane (A) with an aromatic hydrocarbon solvent (B) and an organoaluminum compound (C) to react the alkylaluminoxane (A) with the organoaluminum compound (C) to form the aluminoxane.

2. The process according to claim 1 wherein the alkylaluminoxane (A) is methylaluminoxane having a molecular weight determined by cryoscopic method with benzene of 500 to 4,000.

3. The process according to claim 1 wherein the organoaluminum compound used in the preparation of the alkylaluminoxane (A) is trialkylaluminum.

4. The process according to claim 1 wherein the aromatic hydrocarbon solvent is benzene, toluene, ethylbenzene, xylene or cumene.

5. The process according to claim 1 wherein the organoaluminum compound (C) is an organoaluminum compound having a branched alkyl group.

6. The process according to claim 1 wherein the molar ratio of the organoaluminum compound (C) to the alkylaluminoxane (A) to be reacted is 0.01/1 to 1/1 (in terms of aluminum).

7. The process according to claim 1 wherein the molar ratio of the organoaluminum compound (C) to the alkylaluminoxane (A) to be reacted is 0.01/1 to 0.4/1 (in terms of aluminum).

8. The process according to claim 1 wherein the molar ratio of the organoaluminum compound (C) to the alkylaluminoxane (A) to be reacted is 0.01/1 to 0.09/1 (in terms of aluminum).

9. The process according to claim 1 wherein the concentration of the organoaluminum compound (C) and the alkylaluminoxane (A) in the aromatic hydrocarbon solvent is 0.01 to 5 mol/( (in terms of aluminum).

10. The process according to claim 1 wherein the organoaluminum compound (C) is represented by the formula $$R^1{}_k Al(OR^2)_m H_p X^1{}_q \tag{I}$$

wherein $R^1$ and $R^2$ each represent an alkyl group having 1 to 8 carbon atoms, $X^1$ represents a halogen atom, k represents a number of $0 < k \leq 3$, m represents a number of $0 < m \leq 3$, p represents a number of $0 < p \leq 3$ and q represents a number of $0 < q \leq 3$, with the proviso that $k+m+p+q$ is 3; the aromatic hydrocarbon solvent (B) is benzene, toluene, ethylbenzene, xylene or cumene; and the reaction temperature is $-40°$ C. to $150°$ C.

11. The process according to claim 10 wherein the organoaluminum compound (C) has a branched alkyl group having 3 to 9 carbon atoms.

12. The process according to claim 11 wherein the branched alkyl group is isobutyl.

* * * * *